United States Patent [19]

Clucas

[11] Patent Number: 5,723,721
[45] Date of Patent: Mar. 3, 1998

[54] INBRED CORN LINE CG00685 USE THEREOF

[75] Inventor: Christopher P. Clucas, Washington Court House, Ohio

[73] Assignee: Novartis Corporation

[21] Appl. No.: 567,869

[22] Filed: Dec. 6, 1995

Related U.S. Application Data

[63] Continuation of Ser. No. 393,517, Feb. 22, 1995, abandoned, which is a continuation of Ser. No. 253,191, Jun. 2, 1994, abandoned, which is a continuation of Ser. No. 18,676, Feb. 17, 1993, abandoned.

[51] Int. Cl.$^6$ ............... A01H 5/00; A01H 4/00; C12N 5/04
[52] U.S. Cl. ............... 800/200; 800/250; 800/DIG. 56; 435/412; 435/424; 435/430; 435/430.1; 47/58; 47/DIG. 1
[58] Field of Search .................. 800/200, 205, 800/250, DIG. 56; 47/58, DIG. 1; 435/240.4, 145.49, 50, 412, 424, 430, 430.1

[56] References Cited

PUBLICATIONS

Mumm et al. (1994) A classification of 148 US maize inbreds: I. Cluster Analysis Based on RFLPs. Crop Science 34:842–851.

Mumm et al. (1994) A classification of 148 US maize inbreds: II. Validation of cluster analysis based on RFLPs. 34:852–865.

Sass, John E. (1977) Morphology. In Corn and Corn Improvement. ASA publication #18, 2nd edition. Editor G.F. Sprague. pp. 89–110.

Phillips et al. (1987) *Cell/Tissue Culture and In Vitro Manipulation.* In Corn and Improvement. ASA publication #18. G.F. Sprague et al. editors. pp. 345–387.

Meghji et al. (1984) Inbreeding depression, Inbred and Hybrid Grain Yields, and other Traits of Maize Genotypes Representing Three Eras. Crop Science. Vol. 24, May–Jun. pp. 545–549.

Hallauer et al. (1988) *Corn Breeding.* In Corn and Corn Improvement. ASA publication #18. G.F. Sprague et al. editors pp. 463–564.

Wright, H. (1980) *Commercial Hybrid Seed Production.* In Hybridization of crop plants. Editors W.R. Fehr et al. pp. 161–176.

*Primary Examiner*—Gary Benzion
*Attorney, Agent, or Firm*—Thomas Hoxie

[57] ABSTRACT

According to the invention, there is provided an inbred corn line, designated CG00685. This invention thus relates to the plants and seeds of inbred corn line CG00685 and to methods for producing a corn plant produced by crossing the inbred line CG00685 with itself or with another corn line. This invention further relates to hybrid corn seeds and plants produced by crossing the inbred line CG00685 with another corn line.

15 Claims, No Drawings

INBRED CORN LINE CG00685 USE THEREOF

This application is a continuation, of application Ser. No. 08/393,517, filed Feb. 22, 1995, now abandoned, which is a continuation of Ser. No. 08/253,191, filed Jun. 2, 1994, now abandoned, which is a continuation of Ser. No. 08/018,676 filed, Feb. 17, 1993, now abandoned.

FIELD OF THE INVENTION

This invention is in the field of hybrid corn (*Zea mays* L.) plant breeding, specifically relating to an inbred corn line designated CG00685.

BACKGROUND OF THE INVENTION

Of all the crops produced by U.S. farmers, corn is the crop that has the most economic value. Corn is utilized as livestock feed, as a basis for human consumption, as raw material for industry and as raw material for the production of ethanol. The primary use of farmer produced field corn is for livestock feed. This includes feed for hogs, beef cattle, dairy cows and poultry.

Human consumption of corn includes direct consumption of sweet corn and as snacks after extruder cooking, ground corn eaten as grits, corn meal and corn flour. Corn oil is also used as a high grade cooking oil, salad oil or in margarine. Corn is used in the production of some starches and syrups. Another important use is in the production of sweeteners used in soft drinks.

The wet-milling and dry-milling processes also produce corn starch and corn flour that have applications in industry. Some of these uses include building materials, the paper industry, textiles and starches.

The seed of inbred corn line CG00685, the plant produced by the inbred seed, hybrid seed produced from the crossing of the inbred, the hybrid corn plant grown from said seed, and various parts of the inbred and hybrid corn plant can be utilized for human food, livestock feed, and as a raw material in the industry.

The major reasons for the economic importance of corn and the large acreages planted to the crop are the hybridization of the corn plant and the continued improvement, by researchers, of the genetic stock that is used to produce the seed grown by farmers. This process has been on-going since its beginning in the early part of the century. The average bushel per acre yield for the American farmer has gone from around 30 in the middle of the 1930's (before hybrids became dominant) to the present average of close to 120. While not all of this four-fold increase can be attributed to genetic improvement (availability of relatively cheap nitrogen and improvements in farming practices are two other components), a good share of it can.

Corn is easily hybridized because of the physical distance between the tassel (male part) and the ear (female part). The method of hybridization first involves the development of inbred lines. Inbred corn lines are considered to be homozygous, or, in essence, genetically the same from generation to generation. They are produced by taking the pollen from one plant and putting it only on the ear of that same plant. The resulting seed is grown, selections for uniformity and improved agronomic characteristics are made and the process is repeated until the seeds from the ears of the plants produce homozygous plants and the line is pure. A hybrid is then produced by crossing one inbred with another, genetically different, inbred. The crossing consists of taking the pollen from one inbred and putting it on the ear of the other inbred.

The seed from the crossing of two inbred lines is a first generation hybrid and is called an $F_1$. The $F_1$ of commercially viable hybrids have better yields, and other important characteristics, than either of the parents. This process is called hybrid vigor or heterosis. In succeeding generations ($F_2$, $F_3$, etc.) this heterosis is markedly reduced, making it economically justifiable for the farmer to go back to the seed company and obtain $F_1$ seed each year. As a result, the hybrid corn seed industry benefits both farmers and producers of hybrid corn seed.

The invention of new inbred lines and of new hybrids is extremely important to the companies in the hybrid seed corn industry that have investments in research. Much effort is given to the research and development of these inbreds and hybrids. The breeding and selection of inbred lines to be used as both seed parents and/or pollen parents and which when crossed to other inbred lines produce $F_1$ hybrid seed, which when planted, will produce plants that have characteristics that a farmer desires is a highly specialized skill. It involves many years of inbreeding, skilled selection, correct statistical testing, and decision making.

SUMMARY OF THE INVENTION

According to the invention, there is provided a novel inbred corn line, designated CG00685. This invention thus relates to the seeds of inbred corn line CG00685, to the plants of inbred corn line CG00685 and to methods for producing a corn plant produced by crossing the inbred line CG00685 with itself or another corn line. This invention further relates to hybrid corn seeds and plants produced by crossing the inbred line CG00685 with another corn line.

DEFINITIONS

This section will outline the definitions of terms used herein.

Yield (Bushels/Acre). Yield in bushels/acre is the actual yield of the grain at harvest adjusted to 15.0% moisture.

Percent Moisture. The percent moisture is the actual percentage moisture of the grain at harvest.

Percent Erect. The percent erect, a measure of standability, is the percentage of plants that are not broken below the ear at harvest.

Harvest Roots. Harvest roots is a visual rating. It is based on the number of plants that are root-lodged, i.e.; leaning from the vertical axis at an approximate 30° angle or greater. The ratings range from 1 to 9. A rating of 1 equals no plants root-lodged and a rating of 9 equals all plants root-lodged.

Percent Dropped Ears. The percent dropped ears is the percentage of plants that dropped (lost) their ears before harvest.

Percent Barren Plants. The percent barren plants is the percentage of plants that were barren (lacking ears).

Intactness. Intactness is a visual rating. It is based on the percentage of leaf and stalk matter remaining above the top ear at harvest. The ratings range from 1 to 9. A rating of 1 equals all matter remaining (intact) and a rating of 9 equals all matter gone or the stalk broken over just above the ear.

Percent Green. The percent green is the percentage of the total ear, leaf and stalk matter still green at the time of data collection, approximately physiological maturity.

Standard Index. Standard index gives a single measure of a hybrid's worth based on a linear model utilizing important traits such as yield, percent moisture, standability, percent dropped ears and harvest roots.

DETAILED DESCRIPTION OF THE INVENTION

Inbred corn line CG00685 is a yellow dent/flint corn with superior characteristics and provides a good parental line in crosses for producing first generation ($F_1$) hybrid corn.

Inbred corn line CG00685 was selected for uniformity and agronomic traits using standard pedigree ear-row selection at Washington Court House, Ohio. The inbred was evaluated further as a line and in numerous crosses by the Washington Court House Research Station and other research stations across the central corn belt. Thus the line was evaluated for general and specific combining ability.

The inbred is adapted to the central and southern Illinois, Indiana, Ohio and Pennsylvania. It can be used advantageously in producing hybrids that are from approximately 105 day relative maturity to 125 day relative maturity based on the Minnesota Relative Maturity Rating System for harvest moisture of the grain. The inbred is an acceptable female parent with good seed size distribution. The inbred does not shed a large amount of pollen but has been successfully used as a male parent in seed production. It drys down rapidly and has contributed this trait to all of the hybrid combinations in which it has been tested.

The inbred has shown relative uniformity and stability for all traits as described in the following variety description information. It has been self-pollinated and ear-rowed a sufficient number of generations with careful attention paid to uniformity of plant type to insure relative homozygosity and phenotypic stability. The line has been increased by hand and in isolated fields with continued observations for uniformity. No particular variant traits have been observed or are expected in CG00685.

The inbred CG00685 is a Ciba-Geigy Seed Division (CGSD) proprietary inbred.

Inbred corn line CG00685 can be compared to the public inbred B68. The characteristics of CG00685 versus B68 are summarized below (based primarily on data collected at Bloomington, Ill.):

|  | CG00685 | B68 |
| --- | --- | --- |
| MATURITY | | |
| Days from emergence to 50% of plants in silk | 65 | 72 |
| Heat units from emergence to 50% of plants in silk | 1583 | 1747 |
| Days from emergence to 50% of plants shedding pollen | 64 | 68 |
| Heat units from emergence to 50% of plants shedding pollen | 1553 | 1644 |
| PLANT CHARACTERISTICS | | |
| Plant height to tassel tip (cm) | 201 | 186 |
| Ear height to top ear node (cm) | 78 | 77 |
| Length of top ear internode (cm) | 9 | 9 |
| Ears per stalk | Slight two-ear tendency | Single |
| Number of tillers | None | Slight tendency |
| Anthocyanin in brace roots | Present | Present |
| Cytoplasm type | Normal | Normal |
| LEAF | | |
| Color | Medium green | Medium green |
| Angle from stalk (degrees) | 30–45 | 45 |
| Sheath pubescence | Light | Medium |
| Marginal waves | Few | Few |
| Longitudinal creases | Few | Few |
| Width of ear node leaf at widest point (cm) | 8 | 7 |
| Length of ear node leaf (cm) | 70 | 76 |
| Number of leaves above the ear node | 5 | 7 |
| TASSEL | | |
| Number of lateral branches | 5 | 8 |
| Branch angle from central spike (degrees) | 30–40 | >40 |
| Peduncle length (cm) | 12 | 4 |
| Pollen shed | Medium | Medium |
| Anther color | Purple | Yellow |
| Glume color | Green | Green |
| Glume bars | Absent | Absent |
| EAR (Husked Ear Data at 12.5% Kernel Moisture) | | |
| Length (cm) | 13 | 15 |
| Mid-point diameter (mm) | 36 | 32 |
| Weight (gm) | 60 | 48 |
| Kernel rows | 12, distinct, slightly curved | 12, distinct, straight |
| Silk color | Pink | Pink |
| Husk color (fresh) | Light green | Light green |
| Husk color (dry) | Buff | Buff |
| Husk extension | Long (8–10 cm beyond ear tip) | Very long (>10 cm) |
| Husk leaf | Short (<8 cm) | Short (<8 cm) |
| Shank length (cm) | 12 | 11 |
| Shank (no. of internodes) | 5 | 5 |
| Position of shank (dry husks) | Pendent | Upright |
| Taper | Slight | Slight |
| KERNEL (at 12.5% Kernel Moisture) | | |
| Size (kernels taken from ear midpoint) | 9 mm long 7 mm wide 4 mm thick | 8 mm long 6 mm wide 3 mm thick |
| Shape grade (% rounds) | >80 | 60–80 |
| Pericarp color | Colorless | Red and white Variegated |
| Aleurone color | Homozygous, white | Homozygous, white |
| Endosperm color | Yellow | Yellow |
| Endosperm type | Normal starch | Normal starch |
| Gram weight/100 seeds (unsized sample) | 27 | 25 |
| Test weight (pounds) | 63 | 52 |
| COB Diameter at midpoint (mm) | 23 | 24 |
| Strength | Strong | Weak |
| Color | White | Red |

Disease reaction information for CG00685 are given below:

| | |
| --- | --- |
| Common rust | Moderately Resistant |
| Common smut | Resistant |
| Maize chlorotic dwarf | Resistant |
| Maize dwarf mosaic A | Moderately Susceptible |
| Maize dwarf mosaic B | Moderately Susceptible |
| Southern corn leaf blight | Moderately Resistant |
| Wheat streak mosaic | Resistant |

Heat units calculations are derived by using the following formula: Heat Units equals [Daily Maximum Temperature ($\leq 86°$ F.) plus Daily Minimum Temperature ($\geq 50°$ F.)] divided by 2 minus 50° F.

Electrophoresis results for CG00685 and the public inbred B68 are shown in Table 1 below:

TABLE 1

Electrophoresis results for CG00685 and B68 Alleles Present

| Locus | CG00685 | B68 |
|---|---|---|
| Acp1 | 4 | 3 |
| Adh1 | 4 | 4 |
| Cat3 | 9 | 9 |
| Got1 | 4 | 4 |
| Got2 | 4 | 4 |
| Got3 | 4 | 4 |
| Idh1 | 4 | 4 |
| Idh2 | 6 | 6 |
| Mdh1 | 6 | 6 |
| Mdh2 | 6 | 6 |
| Mdh3 | 16 | 16 |
| Mdh4 | 12 | 12 |
| Mdh5 | 12 | 12 |
| Mmm | M | M |
| Pgm1 | 9 | 9 |
| Pgm2 | 3 | 4 |
| Pdg1 | 3.8 | 2 |
| Pdg2 | 5 | 5 |
| Phi1 | 4 | 5 |
| No. plants | 36 | 9 |

This invention is also directed to methods for producing a corn plant by crossing a first parent corn plant with a second parent corn plant wherein the first or second corn plant is the inbred corn plant from the line CG00685. Further both first and second parent corn plants may be from the inbred line CG00685. Thus, any methods using the inbred corn line CG00685 are part of the invention: backcrosses, hybrid breeding, and crosses to populations. Any plants produced using inbred corn line CG00685 as a parent are within the scope of this invention. Advantageously, the inbred corn line CG00685 is used in crosses with other corn varieties to produce first generation ($F_1$) corn hybrid seed and plants with superior characteristics.

As used herein, the term "plant" includes plant cells, plant protoplasts, plant cell of tissue culture from which corn plants can be regenerated, plant calli, plant clumps, and plant cells that are intact in plants or parts of plants such as pollen, flowers, kernels, ears, cobs, leaves, husks, stalks, and the like. Thus another aspect of this invention is to provide for cells which upon growth and differentiation produce the inbred line CG00685.

The seed of inbred corn line CG00685, the plant produced from the inbred seed, the hybrid corn plant produced from the crossing of the inbred, hybrid seed, and various parts of the hybrid corn plant can be utilized for human food, livestock feed, and as a raw material in industry.

The results in Table 2 compare a CG00685 corn hybrid to Funk G® brand 4626. Both hybrids have a parent in common other than CG00685. Funk G® brand 4626 is currently being sold in the United States and is adapted to most of the same areas as the CG00685 hybrid. The data was averaged across all locations and replications and would include experiments grown by several CGSD corn research programs in 1990 and 1991.

TABLE 2

CG00685 hybrid (#1) compared to 4626 (#2)

| | Yield (BU/A) | Percent Moisture | Percent Erect | Harvest Roots | Percent Dropped Ears |
|---|---|---|---|---|---|
| 1 | 120 | 15.5 | 93.6 | 1.6 | 1.02 |
| 2 | 120 | 17.8 | 94.6 | 1.8 | 0.89 |
| Difference | 0 | 2.3 | 1.0 | 0.2 | 0.13 |
| Locations | 142 | 142 | 123 | 14 | 28 |

| | Percent Barren Plants | Intactness | Percent Green | Standard Index |
|---|---|---|---|---|
| 1 | 10.3 | 6.0 | 32.5 | 179 |
| 2 | 13.2 | 6.4 | 27.4 | 174 |
| Difference | 2.9 | 0.4 | 5.1 | 5 |
| Locations | 11 | 143 | 92 | 180 |

The data show that although CG00685 is earlier than 4626 (percent moisture) both CG00685 and 4626 make hybrids of similar yield. In this and other hybrid combinations, CG00685 has shown outstanding yield performance relative to other commercially sold hybrids of similar maturity.

The results in Table 3 compare a CG00685 corn hybrid to Funk G® brand 4530. Both hybrids have closely related parents in common other than CG00685. Funk G® brand 4530 is currently being sold in the United States and is adapted to most of the same areas as the CG00685 hybrid. The data was averaged across all locations and replications and would include experiments grown by several CGSD corn research programs in 1990 and 1991.

TABLE 3

CG00685 hybrid (#1) compared to 4530 (#2)

| | Yield (BU/A) | Percent Moisture | Percent Erect | Harvest Roots | Percent Dropped Ears |
|---|---|---|---|---|---|
| 1 | 124 | 15.6 | 93.3 | 1.7 | 0.80 |
| 2 | 124 | 17.8 | 96.3 | 2.0 | 0.33 |
| Difference | 0 | 2.2 | 3.0 | 0.3 | 0.47 |
| Locations | 171 | 171 | 154 | 26 | 65 |

| | Percent Barren Plants | Intactness | Percent Green | Standard Index |
|---|---|---|---|---|
| 1 | 7.0 | 5.4 | 38.8 | 171 |
| 2 | 11.5 | 6.0 | 24.4 | 168 |
| Difference | 4.5 | 0.6 | 14.4 | 3 |
| Locations | 19 | 166 | 116 | 232 |

The data show that although CG00685 is earlier than 4626 (percent moisture) both CG00685 and 4626 make hybrids of similar yield. In this and other hybrid combinations, CG00685 has shown outstanding yield performance relative to other commercially sold hybrids of similar maturity.

Inbred seeds of CG00685 have been placed on deposit at the American Type Culture Collection (ATCC), Rockville, Md., 20852, under deposit accession number 75384 on Dec. 16, 1992.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. An inbred corn line designated CG00685 (ATCC designation 75384).

2. Parts of plants of the inbred corn line designated CG00685 of claim 1.

3. The parts of claim 2 wherein the parts are pollen or a seed.

4. A tissue culture of regenerable cells of inbred corn plant CG00685 (ATCC designation 75384).

5. A tissue culture according to claim 4 comprising regenerable cells of the plant selected from meristematic tissue, anthers, leaves, embryos, pollen and protoplasts therefrom.

6. A corn plant regenerated from regenerable cells of the tissue culture of CG00685 having all of the physiological and morphological characteristics of inbred corn plant CG00685 (ATCC designation 75384).

7. A method for producing corn seed comprising crossing a first parent corn plant with a second parent corn plant wherein said first or second parent corn plant is the inbred corn plant having designation CG000685 (ATCC designation 75384).

8. The method of claim 7, wherein said first and second parent corn plants are both from the inbred corn line designated CG00685.

9. A first generation ($F_1$) corn plant and seed thereof produced by growing said corn seed of claim 7.

10. A first generation corn plant and seed thereof produced by growing said corn seed of claim 8.

11. A first generation ($F_1$) hybrid corn plant and seed thereof produced by crossing a first inbred female corn plant with a second inbred male corn plant, wherein said first or second parent corn plant is the inbred corn plant having the designation CG00685 (ATCC designation 75384).

12. The hybrid corn plant and seed thereof of claim 11, wherein said inbred corn plant having the designation CG00685 is the female parent.

13. The hybrid corn plant and seed thereof of claim 11, wherein said inbred corn plant having the designation CG00685 is the male parent.

14. A method for producing first generation ($F_1$) hybrid corn seed comprising crossing a first inbred parent corn plant with a second inbred parent corn plant, wherein said first or second parent corn plant is the inbred corn plant having the designation CG00685 (ATCC designation 75384).

15. A first generation ($F_1$) hybrid corn plant and seed thereof produced by growing said hybrid corn seed of claim 14.

* * * * *